US00PP20311P2

(12) United States Plant Patent
Utecht

(10) Patent No.: US PP20,311 P2
(45) Date of Patent: Sep. 15, 2009

(54) *PELARGONIUM* PLANT NAMED 'GRAVIO'

(50) Latin Name: *Pelargonium×hortorum*
Varietal Denomination: Gravio

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/221,617

(22) Filed: Aug. 5, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Kent L Bell
(74) *Attorney, Agent, or Firm*—S. Matthew Edwards

(57) ABSTRACT

A new *Pelargonium* plant named 'Gravio', particularly distinguished by the stellar-type, red-purple flowers, medium green, distinctly zoned foliage, special leaf shape, vigorous growth, and mounding, moderately tight plant habit with the inflorescences well above the foliage.

2 Drawing Sheets

Latin name of the genus and species of the plant claimed: *Pelargonium×hortorum.*

Varietal denomination: 'Gravio'.

BACKGROUND OF THE NEW PLANT

The present invention comprises a new *Pelargonium,* botanically known as *Pelargonium×hortorum* and hereinafter referred to by the variety name 'Gravio'.

'Gravio' is a product of a planned breeding program. The new cultivar has stellar-type red-purple flowers, medium green, distinctly zoned foliage, and vigorous growth.

'Gravio' originated from a hybridization made in the summer of 2003 in a controlled breeding program in Hillscheid, Germany. The female parent was the variety 'Grasalm', U.S. Plant Pat. No. 16,642, with single-type, rose-red flowers, stellar-type shape, medium green, zoned foliage and medium to tall sized, and mounding plant habit. The plant habit of the parent 'Grasalm' is somewhat smaller than that of 'Gravio'.

The male parent of 'Gravio' was an unpatented hybrid seedling identified as 'k00-5693-12' with rose-red, single-type flowers, relatively light green foliage, weak leaf zone, and medium to tall plant habit.

'Gravio' was selected as one flowering plant within the progeny of the stated cross in the spring of 2004 in a controlled environment in Galdar, Gran Canaria, Spain.

The first act of asexual reproduction of 'Gravio' was accomplished by vegetative cuttings from the initial selection in the fall of 2004 in a controlled environment in Galdar, Gran Canaria, Spain.

Horticultural examination of plants grown from cuttings of the plant initiated in early March of 2005 in Hillscheid, Germany, and continuing thereafter, has demonstrated that the combination of characteristics as herein disclosed for 'Gravio' are firmly fixed and are retained through successive generations of asexual reproduction.

'Gravio' has not been observed under all possible environmental conditions. The phenotype may vary significantly with variations in environment such as temperature, light intensity and day length.

Plant Breeder's Rights for this cultivar was applied for in Germany on Feb. 21, 2007, in Canada on Mar. 30, 2007, and in the European Union on Jun. 20, 2008. 'Gravio' has not been made publicly available more than one year prior to the filing of this application.

DESCRIPTION OF THE DRAWINGS

This new *Pelargonium* plant is illustrated by the accompanying photographic drawings which show blooms, buds, and foliage of the plant in full color. The colors shown are as true as can be reasonably obtained by conventional photographic procedures.

The first photographic drawing shows a flowering potted plant of the new variety.

The second photographic drawing is a close-up view of an inflorescence.

DETAILED BOTANICAL DESCRIPTION

The measurements were taken in Hillscheid, Germany in early May 2007 on plants that were growing in 12 cm pots in a greenhouse spring trial. Culture of these plants had started in early March 2007 with planting of rotted cuttings.

Color chart used: Royal Horticultural Society Colour Chart (R.H.S.) 2001.

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* as a new and distinct variety:

1. Red-purple flower color
2. Stellar-type, single flowers
3. Medium green, distinctly zoned foliage, flabellate leaf shape
4. Vigorous growth, and medium to tall plant size
5. Mounding, moderately tight plant habit with the flower heads well above the foliage
6. Early to medium spring flowering response
7. Suitable as a bedding plant or for container planting
8. Good rain resistance

TABLE 1

DIFFERENCES BETWEEN THE NEW VARIETY 'GRAVIO' AND A SIMILAR VARIETY

| | 'Gravio' | 'Mark's Elf' (Not patented) |
|---|---|---|
| Flower color general view | Red-purple | Slightly more purple hue |
| Color upper petals | N57A at tips, mainly 43B | RHS N57A |
| Color lower petals | N57B to N66B | N66B or lighter |
| Flower size and shape | Larger and more zygomorphic, upper petals are much longer than lower petals | Rounder flower shape, upper and lower petals of similar size |
| Flower length | 5.6 cm | 3.9 cm |
| Inflorescence, diameter | 10.0 cm | 8.3 cm |
| Flowers per inflorescence | 20-30 | 40-60 |
| Leaf size (width) | 7.3 cm | 6.8 cm |

Plant:

*Form, growth and habit.*—Shrub, spreading to mounding with the inflorescences well above the foliage.

*Plant height.*—15.4 cm.

*Plant height (inflorescence included).*—Approximately 24 cm.

*Plant width.*—27.3 cm.

*Plant size at the end of the summer.*—31 cm. (6 months old, August 28).

*Plant width at the end of the summer.*—35–40 cm in diameter.

Stem:

*Number of branches.*—8.5.

*Color of stem.*—RHS 143C to 144A, no anthocyanin.

*Length of stem.*—From 13 cm to 16 cm.

*Diameter.*—0.8–1.1 cm.

*Length of internodes.*—Approximately 1–2 cm.

*Texture.*—Appears smooth, but with fine, dense pubescence.

Foliage:

*Immature, leaf color, upper surface.*—RHS 137C to 137D. Lower surface: RHS 143C.

*Mature, leaf color, upper surface.*—RHS 137D mainly. Lower surface: Between 143C and 144B.

*Length.*—4.5 cm.

*Width.*—7.3 cm.

*Shape.*—Flabellate with distinct lobes, palmate venation.

*Base shape.*—Wide open, nearly truncate.

*Apex shape.*—Rounded.

*Margin.*—Lobes and dentate, somewhat irregular.

*Texture.*—Dull, velvety with very short pubescence.

*Color of zone.*—From RHS 166A to 200C, of medium distinctness.

*Color of veins, upper surface.*—RHS 143B, not very distinct.

*Color of veins, lower surface.*—RHS 145A, light green.

*Petiole, color.*—RHS 143C to 144B, yellowish green.

*Petiole, length.*—Variable, range from 6.5 cm to 11 cm.

*Diameter of petiole.*—0.3 cm.

*Texture.*—Covered with fine pubescence.

Inflorescence:

*Type.*—An umbel, semi-spherically shaped.

*Begin of flowering (50% of plants with open flowers).*—Around April 30 (9 weeks old).

*Duration of flowering.*—Continuous flowering throughout the Summer.

*Number of inflorescences per plant.*—3–5 (at the stated time); 25–30 in late summer.

*Number of flowers per inflorescence.*—About 20–30.

*Umbel diameter.*—10.0 cm.

*Umbel depth.*—6.0–6.5 cm.

*Color of peduncle.*—RHS 143C to 144B, often one side with anthocyanin, RHS 178B.

*Length of peduncle.*—17.3 cm.

*Peduncle diameter.*—0.3 cm.

*Texture.*—A little rough, with short, dense pubescence.

*Color of pedicel.*—Initially green, RHS 144A, turning reddish-brown, RHS 180A.

*Length of pedicel.*—2.9 cm.

*Diameter of pedicel.*—1.5 mm.

*Texture.*—Covered with glandular hair.

Corolla:

*Form.*—Zygomorphic, roughly star-shaped, petals not overlapping.

*Length of flower.*—5.6 cm.

*Width of flower.*—4.7 cm.

*Depth of flower.*—1.3–1.5 cm.

*Number of petals.*—5.

*Color upper petals, upper surface.*—Main part RHS 43B, upper third N57A, at base weak veins RHS 46A.

*Color upper petals, lower surface.*—Towards base RHS 43B, upper part N66B

*Length of upper petals.*—3.0–3.2 cm.

*Width of upper petals.*—0.9 cm.

*Color lower petals, upper surface.*—RHS N57B to N66B, no markings.

*Color lower petals, lower surface.*—RHS N57C.

*Length of lower petals.*—2.6–2.8 cm.

*Width of lower petals.*—1.1–1.2 cm.

*Petal shape.*—Rhomboid, upper petals more elongate.

*Apex shape.*—Acuminate to caudate.

*Margin.*—Mainly entire, yet with a few irregular incisions or crenation in the middle part.

*Petal texture.*—Smooth, glabrous.

*Number of petaloids (if any).*—None.

Bud (just before opening):

*Color.*—RHS N66A to N66B, red-purple.

*Length.*—1.3 cm.

*Width.*—0.5–0.6 cm.

*Shape.*—Elliptic, narrow, somewhat asymmetric.

Calyx:

*Number of sepals.*—5.

*Color of sepals.*—RHS 143C.

*Length of sepals.*—1.1 cm.

*Width of sepals.*—2 mm, respective 3mm for the largest.

*Sepal shape.*—Lanceolate.

*Apex shape.*—Acute.

*Margins.*—Entire.

*Texture.*—Covered with relatively long soft hairs.

Reproductive organs:

*Pistil.*—One.

*Length.*—7–8 mm.

*Style color.*—Approximately RHS 53C.

*Style length.*—3–4 mm.

*Stigma color.*—RHS 47A, reddish.

*Number of stamen.*—7.

*Length of anthers.*—2 mm.

*Anther color.*—RHS 53D.

*Length filaments.*—5–6 mm.

*Color of filaments.*—White at base, main part red: RHS 46B or 53C.

*Pollen amount.*—Moderate/Plenty.

*Color of pollen.*—RHS 28A, orange.

*Fertility/seed set.*—Appears fertile, no seed set observed in the fall of 2006.

Disease/pest resistance: Disease resistance and/or susceptibility has not been observed on this plant.

What is claimed is:

1. A new and distinct variety of *Pelargonium* plant named 'Gravio', substantially as illustrated and described herein.

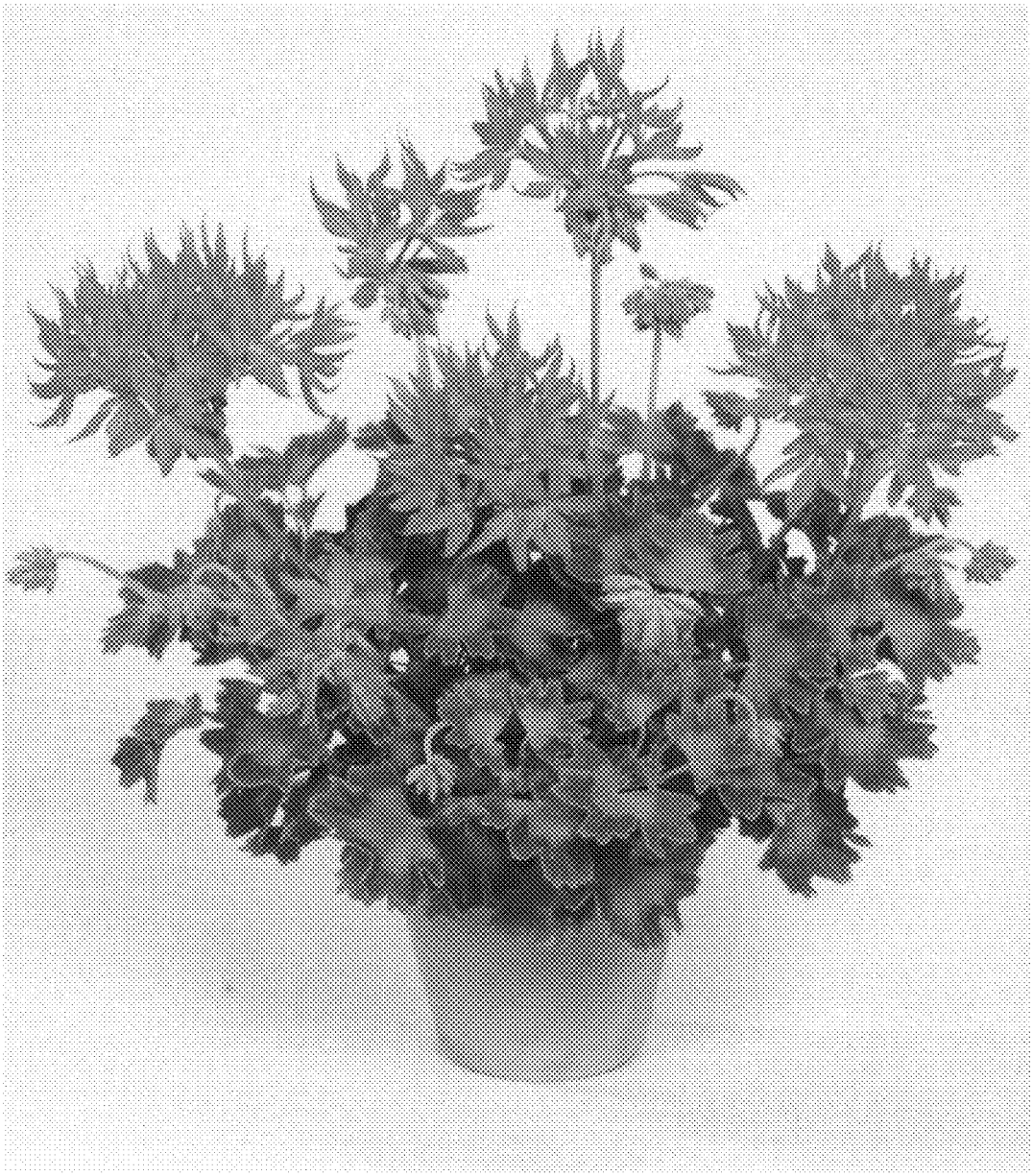

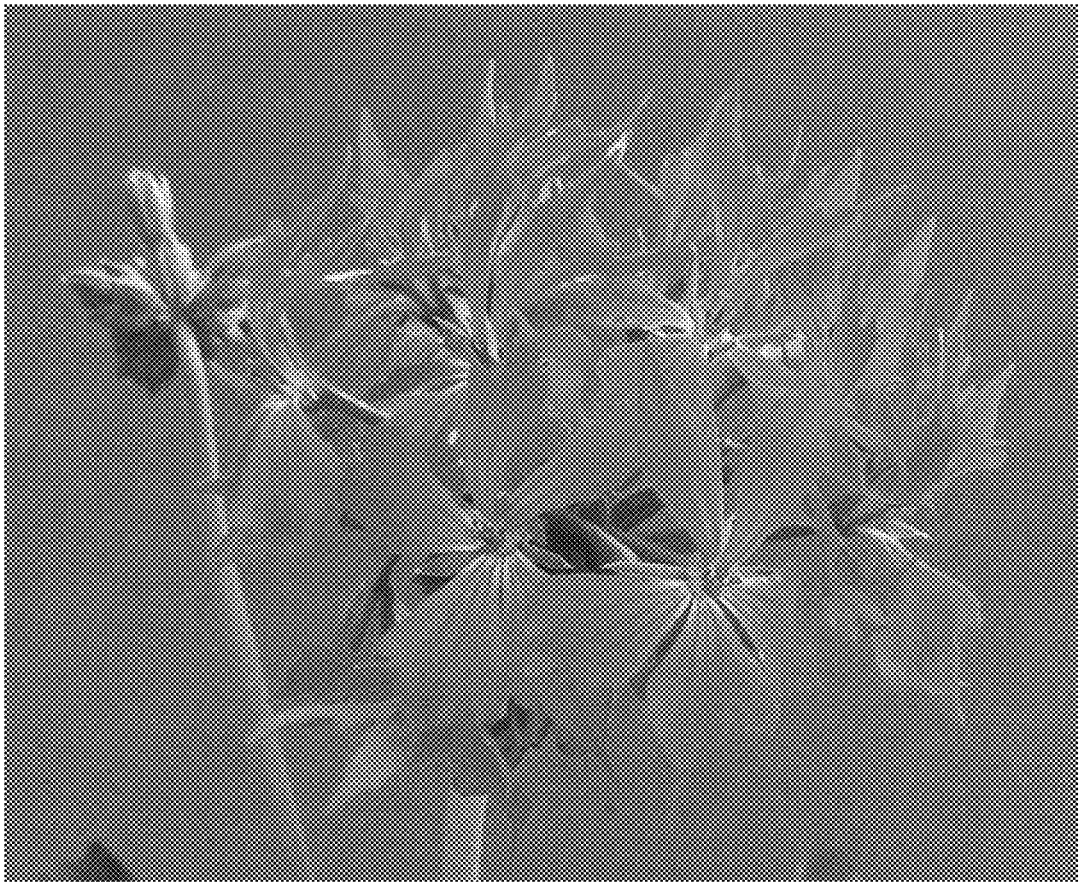

* * * * *